(12) United States Patent
Chou et al.

(10) Patent No.: US 11,105,791 B2
(45) Date of Patent: *Aug. 31, 2021

(54) ELECTRONIC DETECTORS INSIDE NANOFLUIDIC CHANNELS FOR DETECTION, ANALYSIS, AND MANIPULATION OF MOLECULES, SMALL PARTICLES, AND SMALL SAMPLES OF MATERIAL

(71) Applicant: Nanonex Corporation, Monmouth Junction, NJ (US)

(72) Inventors: Stephen Y. Chou, Princeton, NJ (US); Xiaogan Liang, Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/727,911

(22) Filed: Oct. 9, 2017

(65) Prior Publication Data
US 2018/0231520 A1 Aug. 16, 2018

Related U.S. Application Data

(63) Continuation of application No. 12/761,867, filed on Apr. 16, 2010, now Pat. No. 9,810,680.

(60) Provisional application No. 61/170,008, filed on Apr. 16, 2009.

(51) Int. Cl.
| | |
|---|---|
| *G01N 33/487* | (2006.01) |
| *B01L 3/00* | (2006.01) |
| *B82Y 35/00* | (2011.01) |
| *C12Q 1/68* | (2018.01) |

(52) U.S. Cl.
CPC .. *G01N 33/48721* (2013.01); *B01L 3/502761* (2013.01); *B82Y 35/00* (2013.01); *C12Q 1/68* (2013.01); *B01L 3/502707* (2013.01); *B01L 2200/0663* (2013.01); *B01L 2300/0877* (2013.01); *Y10T 436/143333* (2015.01)

(58) Field of Classification Search
CPC ..... B01L 2200/0663; B01L 2300/0877; B01L 3/502707; B01L 3/502761; B82Y 35/00; C12Q 1/68; C12Q 2565/631; Y10T 436/143333; G01N 33/48721
See application file for complete search history.

(56) References Cited

U.S. PATENT DOCUMENTS

2005/0136419 A1* 6/2005 Lee .......................... B82Y 30/00
                                                          435/6.11

OTHER PUBLICATIONS

Lennon et al. "Evaporative Pumping of Liquid in Nanochannel for Electrical Measurement of a Single Biomolecule in Nanofluidic Format", Proceedings of the 7th IEEE, International Conference on Nanotehnology, Aug. 2007, pp. 562-565. (Year: 2007).*

* cited by examiner

*Primary Examiner* — Jennifer Wecker (57) ABSTRACT

The present invention provides methods and apparatus that can manipulate, detect, and/or analyze single molecules, single small particles or single small samples of matter passing through a nanoscale gap within a nanofluidic channel of a detector.

17 Claims, 11 Drawing Sheets

ELECTRONIC DETECTORS INSIDE NANOFLUIDIC CHANNELS FOR DETECTION, ANALYSIS, AND MANIPULATION OF MOLECULES, SMALL PARTICLES, AND SMALL SAMPLES OF MATERIAL

CROSS-REFERENCE TO RELATED APPLICATIONS

The present application is related to, and claims priority from, U.S. Provisional Patent Application Ser. No. 61/170,008 filed on Apr. 16, 2009, which is herein incorporated by reference.

STATEMENT REGARDING FEDERALLY SPONSORED RESEARCH

Not Applicable.

BACKGROUND OF THE INVENTION

The present application is related generally to methods and apparatus for the detection, analysis, and manipulation of microscopic specimens, and in particular, to methods and apparatus to manipulate, detect, and/or analyze samples such as single molecules, single small particles, or small quantities of matter such as DNA as the samples are passed through a nanoscale gap between detector elements in a nanofluidic channel.

There are great needs to detect, analyze and manipulate single molecules, single small particles and single small samples of matter in various fields such as biology, medicine, and pharmaceutical research. The biological species include DNA, proteins, enzymes, and other bio-molecules which have an extremely small volume. In detection, sometimes a single molecule resolution of a single DNA base pair is needed. Often these molecules and small particles are in solution. Existing devices for measurement and analysis of small bio-molecules such as DNA have limitations. For example, devices which rely upon pulling strands of molecules through nanopores and measuring the ionic current through the nanopore caused by the blockage of DNA suffer from poor confinement of the DNA strand within the nanopore and noise effects caused by the movement of the unrestrained portions of the DNA strand outside of the nanopore. These devices additionally rely upon the DNA blockage of ionic current through the nanopore, which is an electrical signal along the DNA backbone, and which depends both on the DNA base pairs within the nanopore, as well as some DNA base pairs which are outside of the nanopore and are subjected to random movement. As such, these devices may be unable to sufficiently resolve two adjacent DNA bases.

The present invention overcomes certain current limitations and offers unique capabilities and performance, including ultra-fast real-time and label-free analysis (e.g. sequencing) of an individual strand of DNA.

BRIEF SUMMARY OF THE INVENTION

Briefly stated, the present disclosure provides in a first embodiment a method for manipulating, detecting, and/or analyzing single molecules, single small particles, or single small samples of matter. The method requires drawing the sample into a nanofluidic channel. As the sample moves through the nanofluidic channel, it is stretched into a linear chain and constrained to pass through at least one nanogap within the nanofluidic channel. Signals representative of an environmental characteristic in the region of the nanogap, such as an electrical or optical characteristic, are observed to identify changes resulting from the presence or absence of the sample in the nanogap as is moves through the nanofluidic channel.

In an additional embodiment, the present disclosure provides an apparatus that can manipulate, detect, and/or analyze single molecules, single small particles or single small samples of matter. The apparatus or nanogap detector consists of a fluidic channel through which matter samples can be drawn. At least one pair of detector elements, such as nanowires, form a nanogap across the fluidic channel, through which the matter samples must pass. The size of the nanogap is selected based on the molecular size of the matter samples to be observed with the apparatus, and as such, permits only a single matter sample to pass through the nanogap at a time. Signals from the detector elements are observed to identify changes in the environmental characteristics within the nanogap resulting from the presence of a matter sample. These environmental characteristics may be electrical or optical.

In an additional embodiment, the present disclosure provides a method for the manufacture of a nanogap detector suitable for manipulating, detecting, and/or analyzing single molecules, single small particles, or single small samples of matter. The fabrication method includes the formation of at least a single nanofluidic channel on a substrate, fabrication of a narrow trench in a resist layer disposed over the substrate, aligned normal to the nanochannel for a subsequent lift-off of metals to form the metallic nanowires and a nanogap within the nanochannel. After exposing the substrate surface by removing the resist residual layer a metal nanowire pair is fabricated within the nanogap inside the nanochannel. Finally, the nanogap detector is sealed by pressing a thin cover slip, which was coated with a thin conformable adhesion layer, on top of the substrate, enclosing the nanofluidic channel, nanogap, and nanowires.

The foregoing features, and advantages set forth in the present disclosure as well as presently preferred embodiments will become more apparent from the reading of the following description in connection with the accompanying drawings.

BRIEF DESCRIPTION OF THE SEVERAL VIEWS OF THE DRAWINGS

In the accompanying drawings which form part of the specification.

Corresponding reference numerals indicate corresponding parts throughout the several figures of the drawings. It is to be understood that the drawings are for illustrating the concepts set forth in the present disclosure and are not to scale.

Before any embodiments of the invention are explained in detail, it is to be understood that the invention is not limited in its application to the details of construction and the arrangement of components set forth in the following description or illustrated in the drawings.

DETAILED DESCRIPTION

The following detailed description illustrates the invention by way of example and not by way of limitation. The description enables one skilled in the art to make and use the present disclosure, and describes several embodiments, adaptations, variations, alternatives, and uses of the present disclosure, including what is presently believed to be the best mode of carrying out the present disclosure.

The present invention is related to methods and apparatus 10 that can manipulate, detect, and/or analyze single molecule, single small particle or single small sample of matter. The devices 10 have two key components: (a) nanofluidic structures; and (b) detection (sensing) structures associated with a nanogap constriction within said nanofluidic structure. The two components can be combined in various ways to create different functions in manipulation, detection and analysis.

Figure 1:
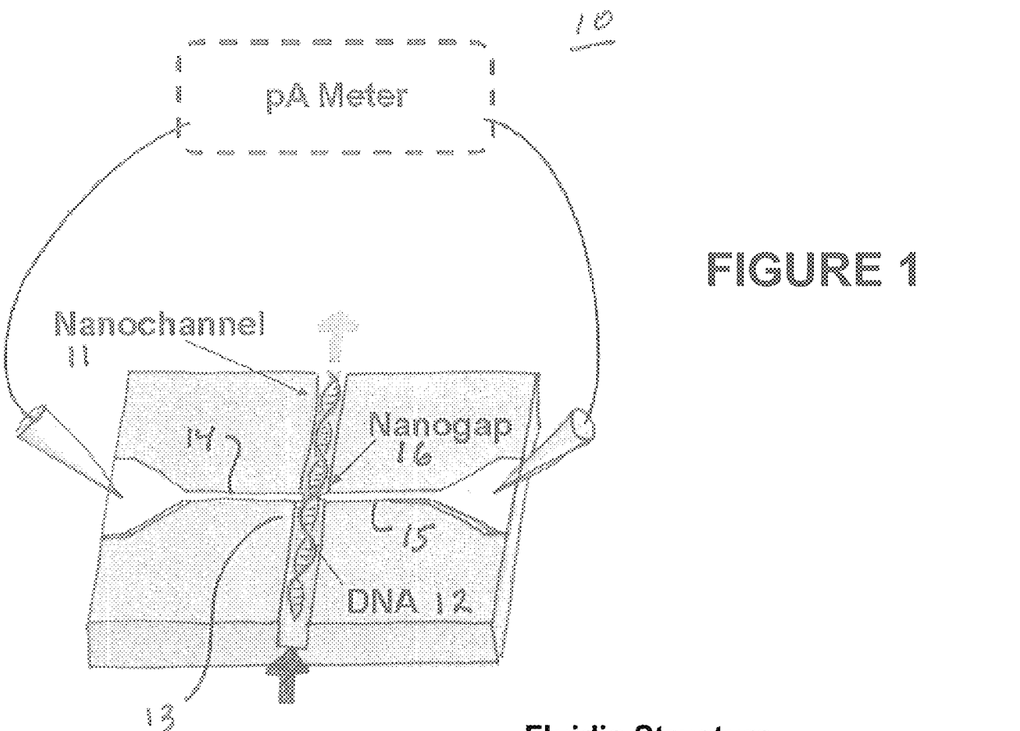
FIG. 1 is a perspective illustration of a DNA detector of the present disclosure with a nanogap inside a nanofluidic channel.
Figure 2:
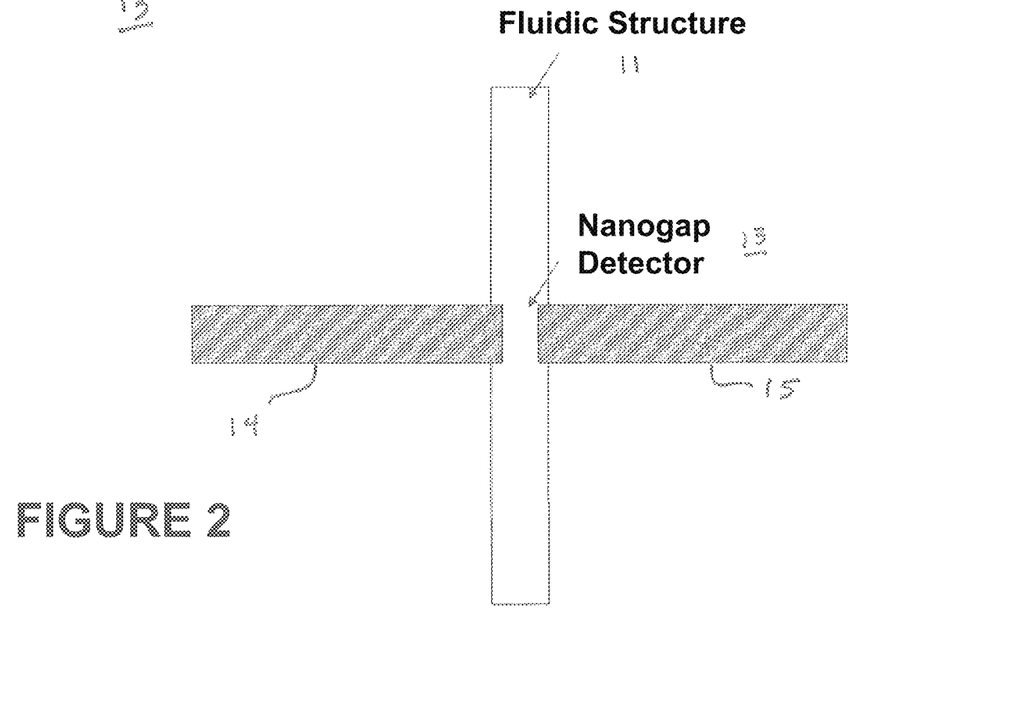
FIG. 2 is a schematic illustration of the DNA detector of FIG. 1.
Figure 3A:
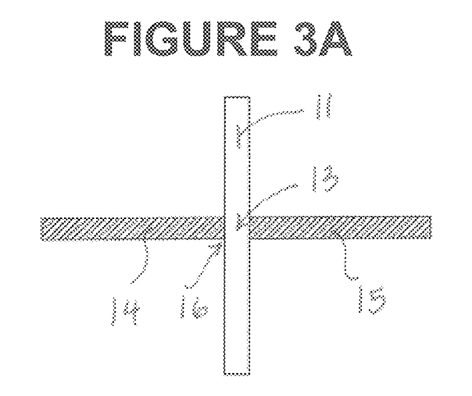
FIGS. 3A-3E provide sectional illustrations of alternate embodiments for the DNA detector of FIG. 1.
Figure 3B:
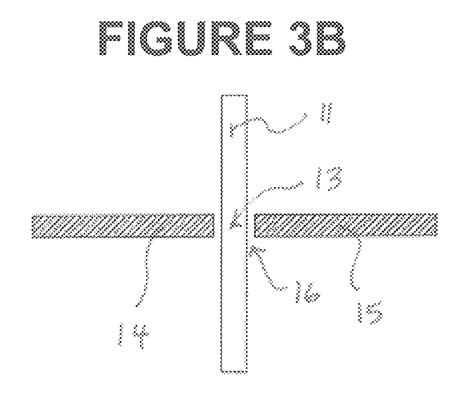
Figure 3C:
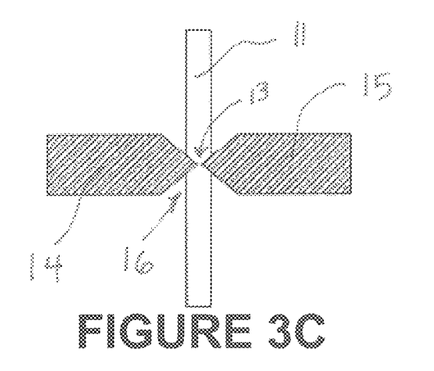
Figure 3D:
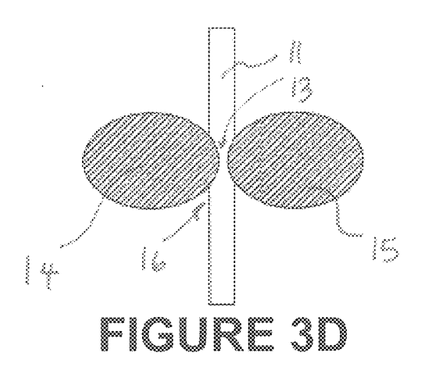
Figure 3E:
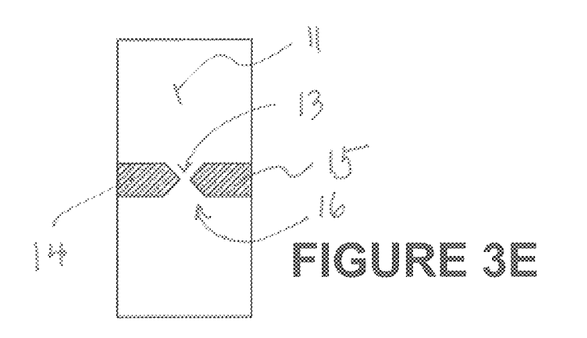
Figure 4A:
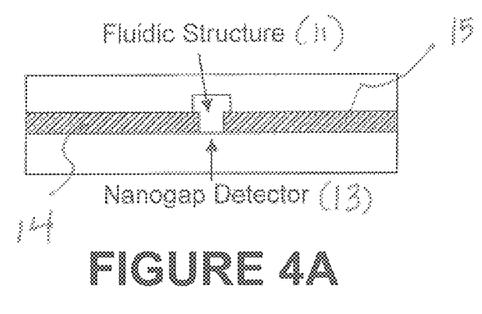
FIGS. 4A-4F provide cross-sectional illustrations of alternate embodiments for the DNA detector of FIG. 1.
Figure 4B:
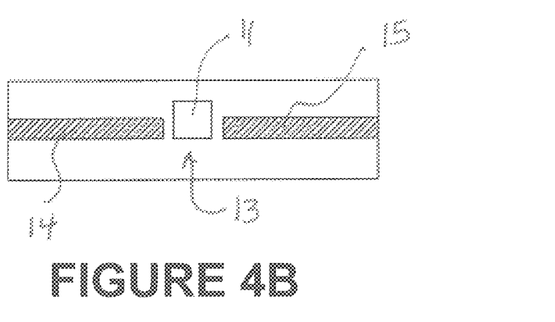
Figure 4C:
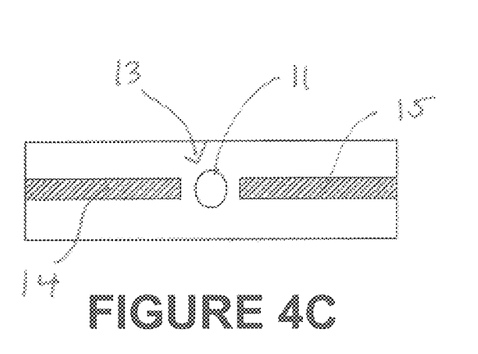
Figure 4D:
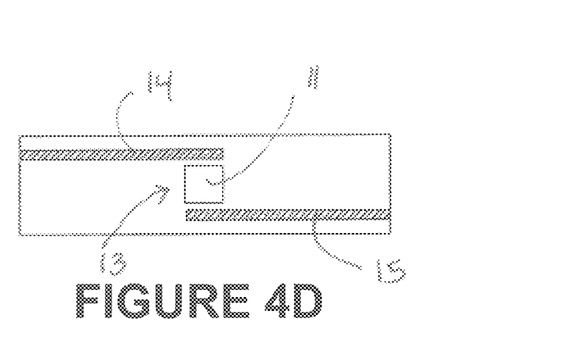
Figure 4E:
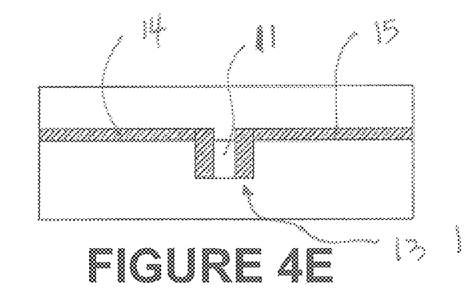
Figure 4F:
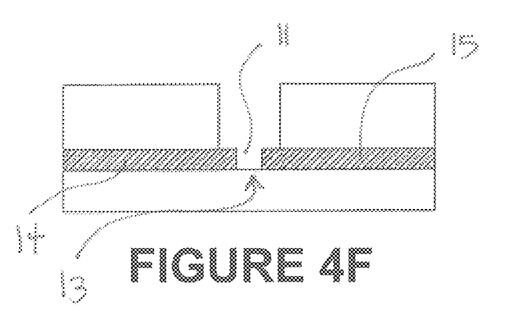

In an embodiment of the present disclosure shown at FIGS. 1 and 2, a single long nanofluidic channel is shown with a nanogap detector disposed inside the nanofluidic channel. The detector 10 employs the long nanofluidic channel 11 to stretch a biomolecule, such as a DNA strand 12, into a linear chain, while using the nanogap detector 13, comprising a pair of metal nanowires 14 and 15 separated by a gap 16 (which may be as small as 9.0 nm), to measure electrical conduction perpendicular to the backbone of the molecule strand as it passes through the gap 16. When the sample molecules are driven through the fluidic structure and pass the nanogap 16, various electrical signals can be obtained through the nanowires 14 and 15 for identifying or analyzing the sample molecules as they pass through the gap 16. The introduction of sample molecules inside the fluidic structures can noticeably limit the number of molecules within the measurement site (e.g. volume of focus for optical measurement), which can realize the single molecule detection resolution, and also suppress the detection noise associated with thermal fluctuation if the sample molecules are presented to a detector in a bulk solution. The detector 10, termed a "nanogap detector" has demonstrated label free detection of single strands of a DNA molecule, when the strand is flowed inside the nanofluidic channel as shown in FIG. 1, with the results described by Liang and Chou at "Nanogap Detector Inside Nanofluidic Channel For Fast Real-Time Label-Free DNA Analysis" at ACS Nano Letters 2008, Vol. 8 (5), pp. 1472-1476, which is herein incorporated by reference.

The specific configuration of the nanogap 16 formed between the nanowires 14 and 15, and it's relationship to the nanofluidic channel 11 may be varied, as is seen in the schematic plan illustrations of FIGS. 3A-3D and the schematic cross-sections shown in FIGS. 4A-4F.

Fluidic Structures

The nanofluidic structure 11, a key component of the nanodetector 10 can be a single nanochannel as shown in FIGS. 1-4, or multiple nanochannels routed in parallel or connected in various ways. A single nanochannel also can be connected, at the different location of the single channel, to multiple channels to perform different fluidic functions. A nanofluidic channel can have different cross-sections as seen in FIGS. 4A-4F, which can be different shapes (see for example, FIGS. 4C and 4D), or uniform cross-section along the length of the nanochannel or various different cross-section shape along the length of the nanochannel. The nanochannels can be nanofluidic channels, nanoslit channels, open fluidic channels as seen in FIGS. 4E and 4F, or enclosed nanotubes as seen in FIG. 4C. Nanopores can be added to different location of a nanochannel. The materials of fluidic structures can be metals, insulators, or semiconductors or ceramics, such as silicon oxide, silicon, glass, quartz, fused silica, UV curables, polymers, and other ceramic materials.

Electronic Detectors

The electronic detectors 16 inside or adjacent to the nanofluidic channel can include nanogap detectors, transistors, conductors, or diodes. The nanogap detector has two electrodes or nanowires 14 and 15, separated by a gap 16 allowing a fluid flow through the nanochannel through the gap (FIGS. 1-4). The electrical signal is preferably detected by measuring conductance (resistance) or capacitance. The electrical signal may come from electron or ion transport or tunneling current. The nanogap detector materials 14 and 15 can be metals, semiconductors, or nanomaterials such as carbon nanotube, silicon nanowires, and semiconducting or conducting organic materials. The transistors can be small MOSFETs, biopolar transistors, or single electron transistors or memories.

Figure 5:
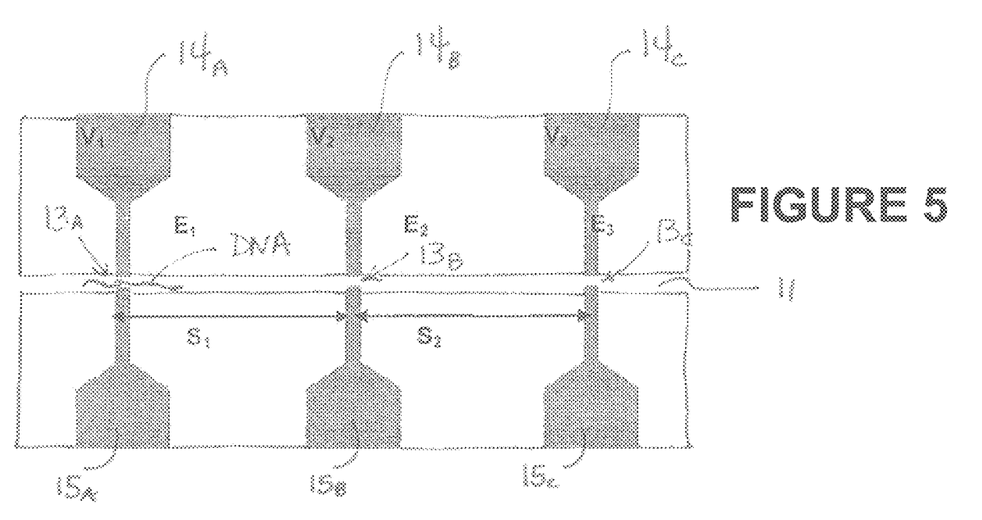
FIG. 5 is an schematic plan view of an alternate embodiment of the nanogap detector of the present disclosure having multiple nanogaps across a nanofluidic channel.
Figures 6A, 6B, 6C, 6D, 6E:
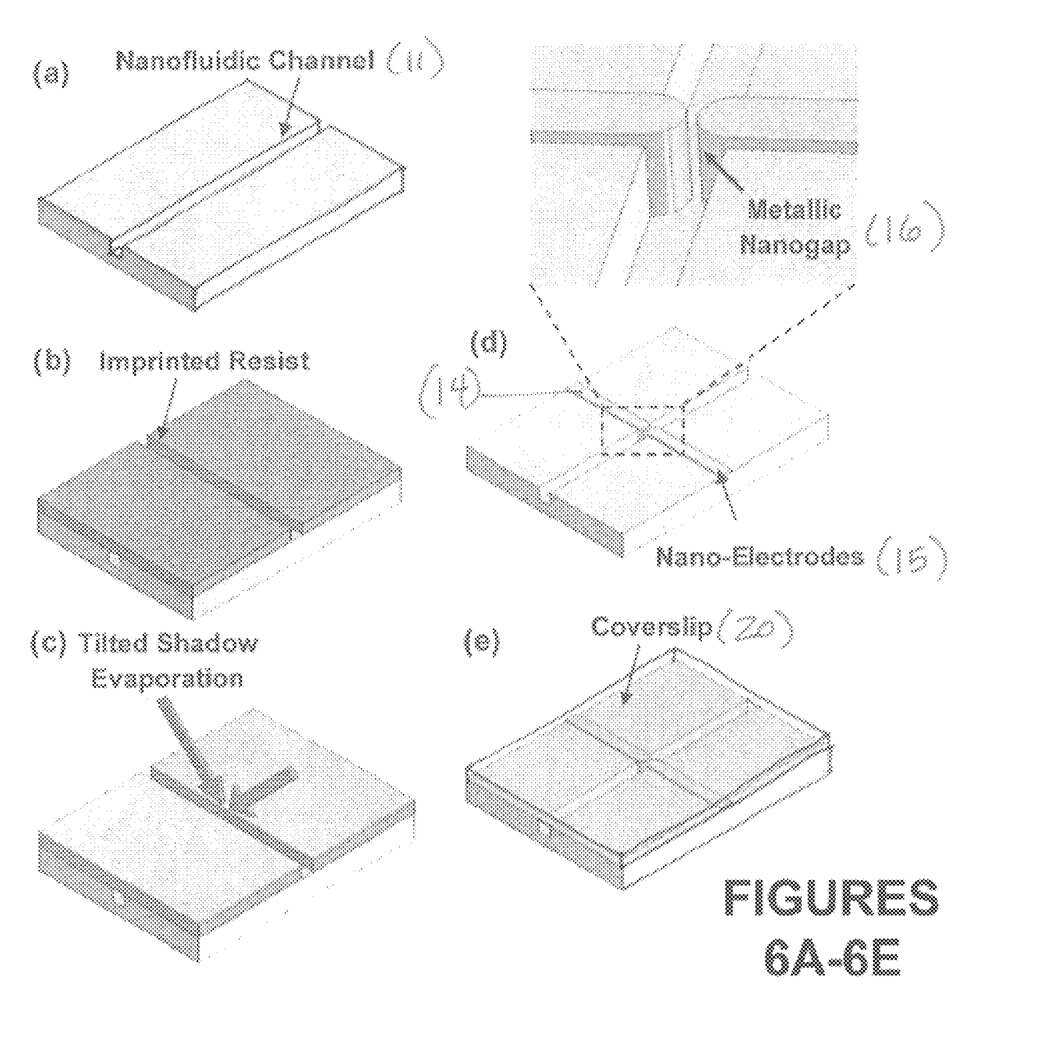
FIGS. 6A-6E illustrate the steps of (a) fabrication, (b) imprinting, (c) deposition, (d) nanowire formation, and (e) sealing in the fabrication of a nanogap detector of the present disclosure.

The electronic detectors can be arranged across a nanofluidic channel as seen in or along a nanofluidic channel. It is also possible to have multiple nanoelectronic devices in a nanofluidic channel, as seen in FIG. 5. For examples, multiple pairs of nanogap detectors 14a-15a, 14b-15b, and 14c-15c can be built in a single nanofluidic channel 11. Each nanogap detector can be used to measure an electrical signal in parallel. A nanochannel detector with multiple electrodes 14a-14c and 15a-15c also allows the detection of the existence, length, and flow speed of a single molecule, single particle, or single small sample of matter. Those of ordinary skill will recognize that any detecting device capable of observing environmental conditions associated with the nanogap may be utilized, including transistors, resistors, nanowires, optical sensors, and biological probes. For example, instead of operating in an electrical measurement mode as described above, a nanogap devices 16 can be configured for optical (Raman, FTIR etc.), magnetic, or other biospecific interactions and detections by replacing the specific elements 14 and 15 on opposite sides of the nanogap with suitable detecting elements capable of observing the desired environmental condition in the nanogap.

Cap Sealing Materials

In the fabrication of nanodetectors, it is often the case that the nanofluidic devices 11 and the nanoelectrical devices 14 and 15 are fabricated on a substrate such as fused quartz first. Then a sealing cover 20 or sealing materials are applied to seal the top of nanofluidic channels and other part of the devices. The sealing cover 20 can be made of materials that are transparent (i.e. glass) or opaque, insulators, semiconductors or metals. The sealing materials can be curable polymers. The viscosity of the polymers can be controlled to meet a sealing condition, such as sealing without blocking the nanofluidic channel 11.

Fabrication of Nanogap Detectors Inside Fluidic Structures

In one fabrication method, such as illustrated in FIGS. 6A-6E, the individual nanogaps 16 can be fabricated inside a fluidic structures 11 by first patterning the nanogap feature; and then depositing the nanogap materials. The lithography techniques used for patterning the nanogap can be e-beam lithography, nanoimprint lithography, focused ion beam, scanning probe lithography, and photolithography. The nanogap materials could be metals, semiconductors, or nanomaterials such as carbon nanotube, silicon nanowires, and semiconducting or conducting organic materials.

Figure 7:
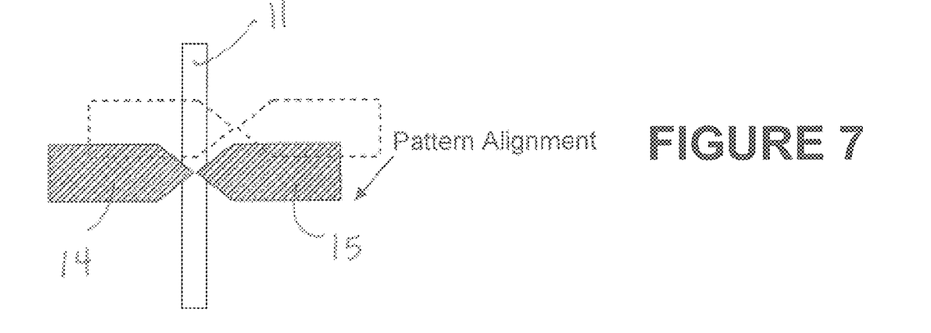
FIG. 7 illustrates the step of pattern alignment in the fabrication of a nanogap detector of the present disclosure.
Figure 8:
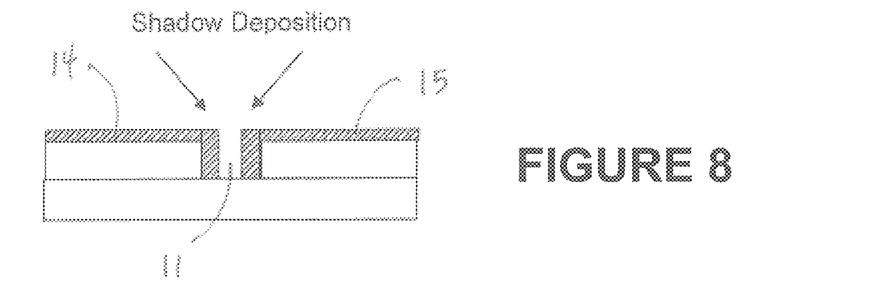
FIG. 8 illustrates the step of deposition in the fabrication of a nanogap detector of the present disclosure.
Figure 9:
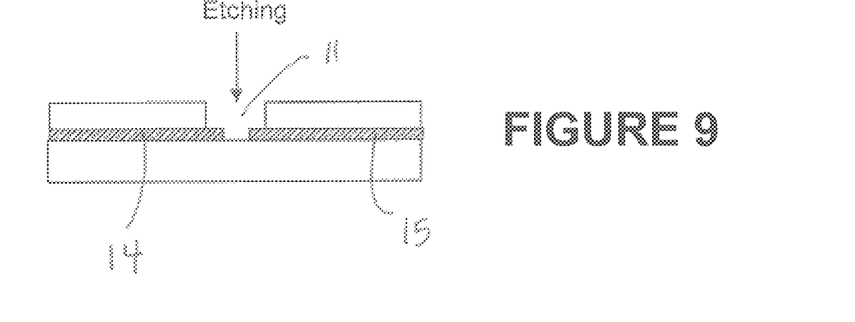
FIG. 9 illustrates the step of etching in the fabrication of a nanogap detector of the present disclosure.

A step involved in the device fabrication is the precise formation of at least a single nanogap 16 into the detection site of a fluidic device 11 (e.g. the middle of a single nanofluidic channel). The possible fabrication schemes can include (1) direct alignment of nanogap feature with the fluidic structures, as shown in FIG. 7; (2) self-alignment of nanogap structures into a fluidic channel by using symmetrical shadow evaporation of the nanogap materials as shown in FIG. 8, and (3) selective etching of the nanogap inside the fluidic device, as shown in FIG. 9.

Figure 10:
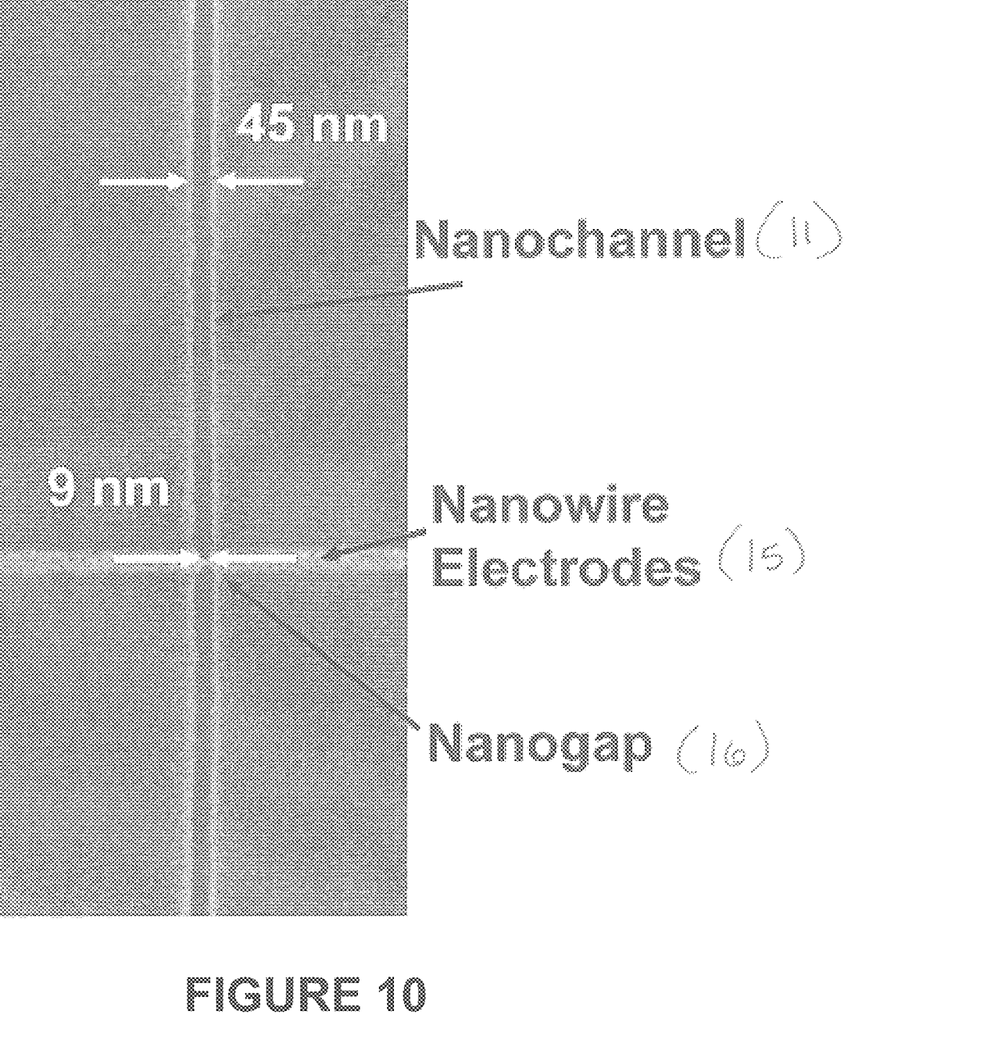
FIG. 10 is a top-view scanning electron micrograph of a nanogap detector without top sealing layer.
Figures 11A, 11B, 11C:
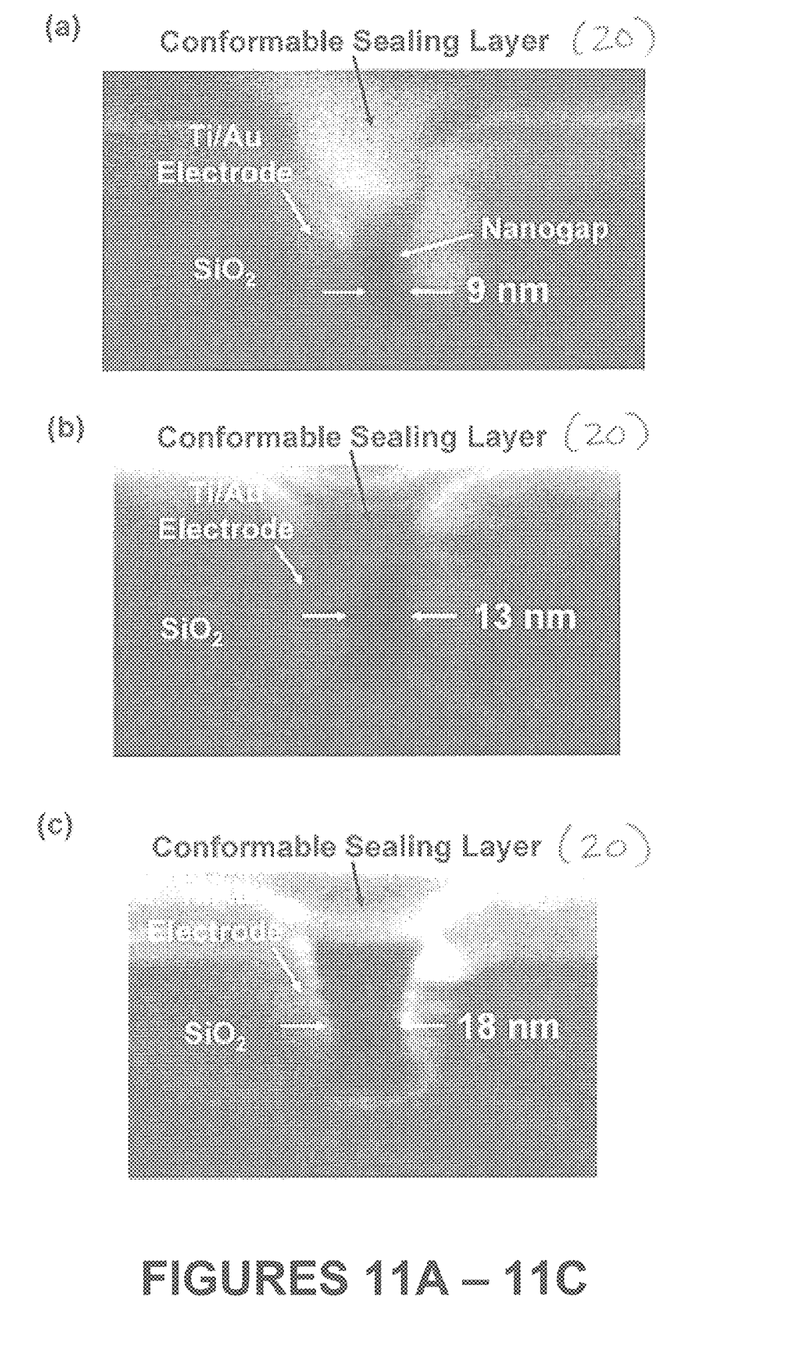
FIGS. 11A-11C are scanning electron micrographs of three different cross-sections (gap×height) of sealed nanogap detectors. (a) 9 nm (gap)×16 nm (height), (b) 13 nm×26 nm, and (c) 18 nm×35 nm.

FIGS. 10 and 11A-11C illustrate examples of the fabrication of a self-aligned metallic nanogap in the middle of a single nanofluidic channel. The nanogap detectors are fabricated on a fused silica substrate by using two lithography steps (first a nanofluidic channel, and second a metallic nanowire pair with a nanogap inside the channel), etching, metal shadow evaporations, and sealing. The mold used for the nanochannel fabrication was fabricated by a nanolithography approach such as e-beam lithography, nanoimprint lithography, focused ion beam, or scanning probe lithography, followed with the etching step (reactive ion etching, ion milling, or wet etching etc.). The mold for making metallic nanowires was patterned by electron-beam lithography (EBL). FIG. 10 illustrates a top-view scanning electron micrograph of a exemplary nanogap detector without top sealing plate. This typical nanogap detector has a fluidic channel of 50 micrometers length, 45 nm width and 45 nm depth, and a pair of metal nanowires of 45 nm width, 18 nm thickness and different gap sizes and gap-heights that vary from 20 to 9 nm and from 30 nm to 16 nm respectively. FIGS. 11A-11C illustrate scanning electron micrographs of three exemplary cross-sections (gap×height) of sealed nanogap detectors. (a) 9 nm (gap)×16 nm (height), (b) 13 nm×26 nm, and (c) 18 nm×35 nm.

The key steps in the nanogap device fabrication illustrated in FIGS. 6A-6E include (FIG. 6a) the fabrication of a single nanofluidic channel 11 on a fused silica substrate using nanolithography and RIE (in this step, micro inlet and outlet were also fabricated using photolithography and RIE, and accessing holes were drilled); (FIG. 6b) fabrication of a narrow trench in resist using another lithography step aligned normal to the nanochannel for a subsequent lift-off of metals to form the metallic nanowires 14 and 15, and the nanogap 16; (FIG. 6c) after exposing the substrate surface by removing the resist residual layer (e.g. that left by nanoimprint process), fabrication of a metal nanowire pair with a nanogap inside the nanochannel by using double shadow evaporations of metal and a lift-off in a solvent (the method makes the nanogap precisely self-aligned inside the nanochannel, and narrows the DNA passage at the gap region); (FIG. 6d) fabrication of metal contacts to the nanowires; and (FIG. 6e) sealing of the top of the nanochannel by pressing a thin cover slip 20, which was coated with a thin conformable adhesion layer, on top of the substrate.

Electrical Measurement Configurations

Figure 14:
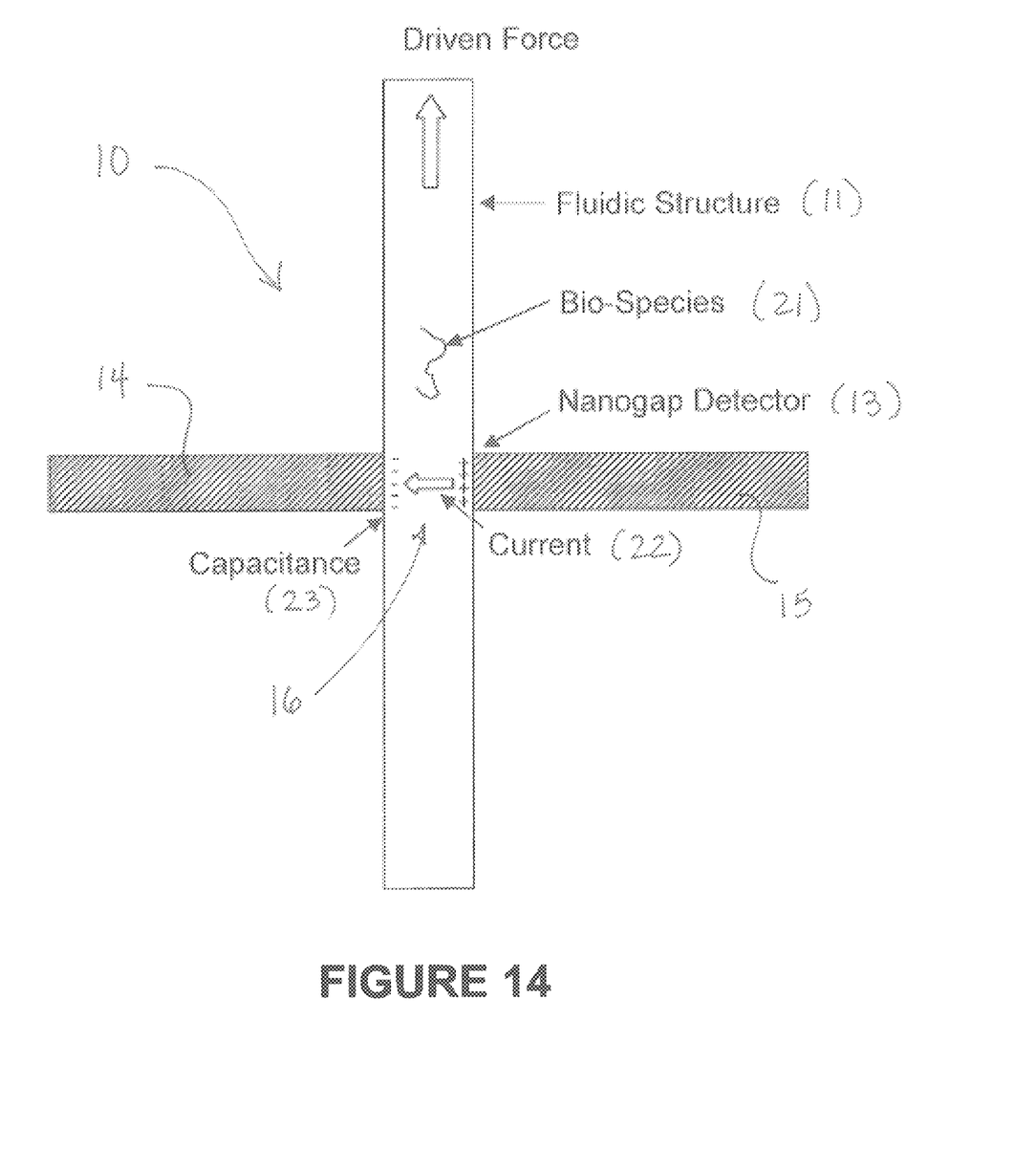
FIG. 14 illustrates the operation of a nanogap detector of the present disclosure.

Referring to FIG. 14, the nanogap detectors 10 illustrated herein can be used to measure various electrical and optical signals associated with passing a bio-species 21 in a solution liquid that is confined in a micro- or nanofluidic device 11. The bio-species (e.g. DNA strands) can be driven in the fluidic devices 11 by applying an external driving force across the fluidic channel, which includes electrophoretic force or hydrodynamic force (e.g. a pressure difference across a nanofluidic channel). When the bio-species passes through the nanogap site 16 in the fluidic structure 11, the presence of the bio-species 21 induces time-dependent electrical or optical signals in the nanowires 14 and 15 (or other suitable signal communication means) that can be recorded to identify or analyze the bio-species 21 The possible electrical signals can be the change of the ionic current 22 across the fluidic channel 11, tunneling current across the backbone of the bio-materials 21, or the change of the nanogap capacitance 23 between the nanowires 14 and 15. The optical signals can be Raman spectra, plasmonic frequencies, or fluorescent signals observed by suitable optical detectors in place of the nanowires 14 and 15.

The electrical signal measures can provide information of the existence, length and flow speed of single molecule, single particle, or single small matter, in the fluidic channel nanogap 16, as well as molecular or atomic structures, physical and chemical function of these matters.

Figure 12A:
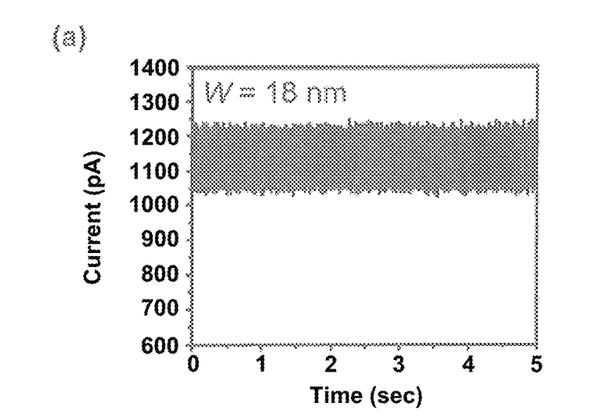
FIGS. 12A-12C graphically illustrates electrical measurements of DNA in three nanogap detectors with different gap sizes.
Figure 12B:
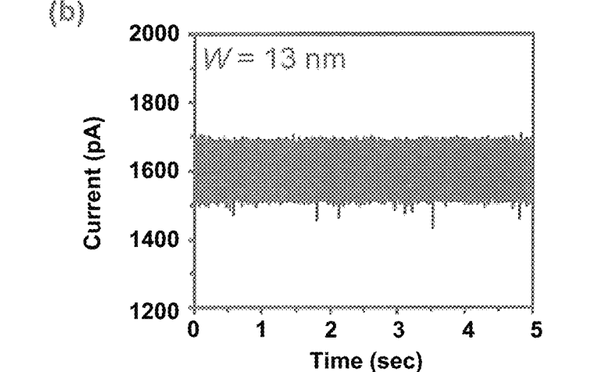
Figure 12C:
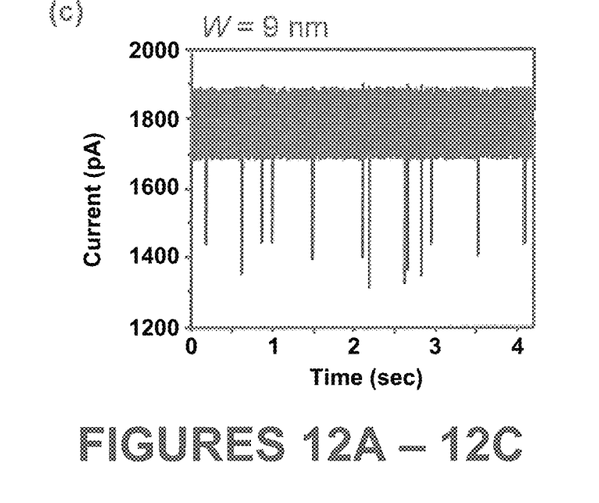

FIGS. 12A-12C graphically illustrate signals obtained from nanogap detectors built inside fluidic devices of various sizes which have been successfully fabricated and used to demonstrate the real-time, label-free DNA detection. For a nanogap device 10 with a gap cross-section of 18 nm (gap)×35 nm (height), as shown in FIG. 12A, there was no any detectable difference in the measured electrical current signals between the pure buffer solution and the buffer solution containing 1.1 kbp of DNA (The average current background current is 1,140 pA caused by solvent conductivity and the noise is ~50 pA rms due to the ampere meter used). For a nanogap device 10 with a 13 nm (gap)×26 nm (height), as shown in FIG. 12B, clear negative pulses were observed only in the buffer solution containing the 1.1 kbp DNAs, but not in the pure buffer solution. Finally, for a nanogap device having a 9 nm (gap)×16 nm (height), as shown in FIG. 12C, the average magnitude of negative pulses increases by ~200% and becomes ~350 pA.

Figure 13A:
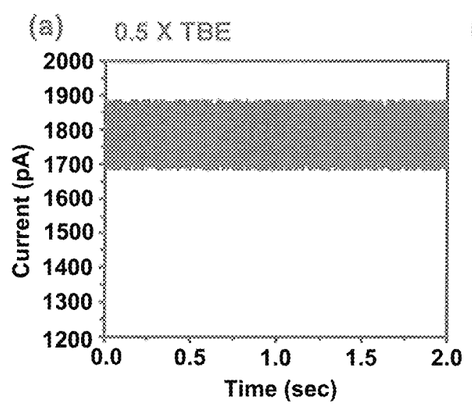
FIGS. 13A-13E graphically illustrate various electrical measurements of targets using a nanogap detector of the present disclosure.
Figure 13B:
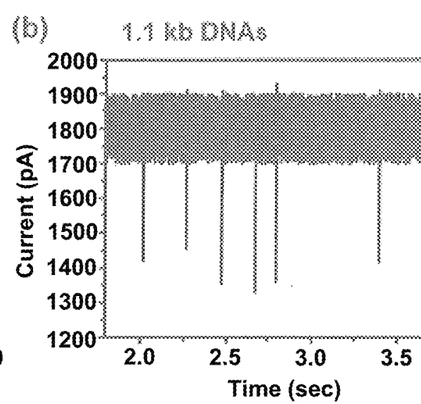
Figure 13C:
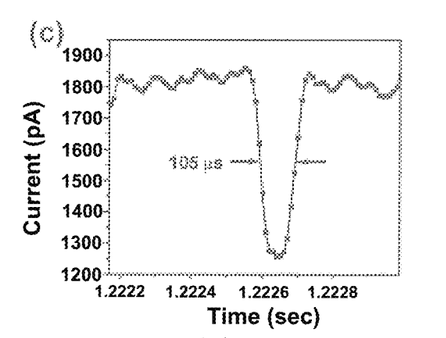
Figure 13D:
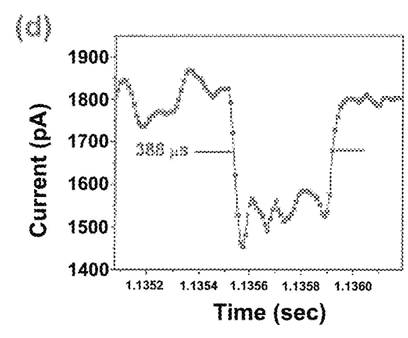
Figure 13E:
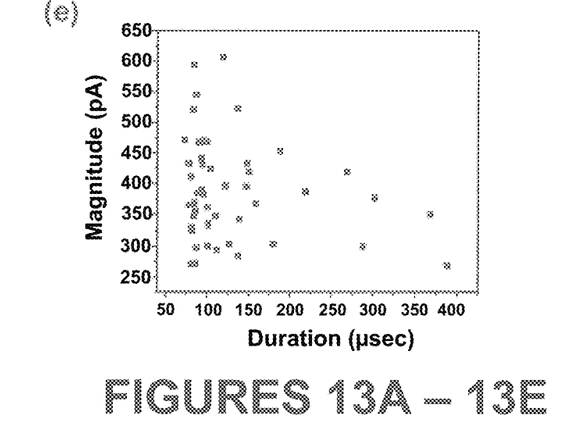

Similarly, FIGS. 13A-13E illustrate electrical measurements by a nanogap detector 10 with a cross-section of 9 nm (gap)×16 nm (height). As shown in FIG. 13A, no any negative pulse train was observed in a pure 0.5× TBE buffer solution; but as seen in FIG. 13B, the pulse trains were detected when 1.1 kbp ds-DNAs were added into the solution. FIG. 13C illustrates an obtained signal with a duration of ~100 μs in an expanded time scale, while FIG. 13D illustrates an obtained signal with a duration of ~388 μs. FIG. 13e illustrates the distribution of pulse durations and amplitudes for 50 pulses.

In general, during the use of a nanogap detector 10 of the present invention for electrical measurement, a DNA strand electrophoretically stretched through the nanogap 16 in the fluidic nanochannel 11 will induce a transient reduction of the ionic current across the metallic gap 16 between the nanowires 14 and 15. This is consistent with the fact that the DNA backbone is more insulating that the buffer solution filled into the nanofluidic channel. This kind of electrical signals can be used to study the DNA properties including total contour length, elasticity, and backbone charge density. All of these parameters are useful for finally realizing the fast label-free DNA sequencing. It is worth to note that DNAs are usually fully stretched into a linear configuration before the on-site detection at the metallic nanogap, which is also a critical step for completely detecting the information of single bases along the DNA backbone.

The main purpose of using nanofluidic devices 10 is to confine the biological species such as DNAs, proteins, or enzymes, etc. into an extremely small volume so that any detection or analysis will have a single molecule resolution. However, in order to realize real-time, label-free bio-detection in such fluidic devices, such as fast DNA sequencing, additional active devices are needed to be built inside the fluidic devices 11. The active devices include transistors, resists, nanowires, optical sensors, or biological probes, etc. The nanogap detector 10 of the present disclosure realizes the real-time, label-free bio-detection, in which a single or multiple nanogaps 16 are fabricated inside a nanofluidic channel 11 and enable the transverse detection (electrical or optical) of bio-species (e.g. DNAs).

As one of embodiments of proposed nanogap detectors in fluidic structures, a metallic nanogap detector inside a nanofluidic channel has been successfully employed to perform real-time label-free measurement of transverse current across a single DNA backbone. The transverse current could be ionic current, residual current in the buffer solution, or tunneling current through bio-species. It is contemplated that this device may be further developed into the next-generation DNA sequencer, which can completely sequence the human being's genomes in hours and at low cost (<$1,000/person) and will have a broad application in illness diagnosis and medicine design, etc.

In one embodiment, the present disclosure provides a method for sampling molecules, small particles or small samples of material which comprises drawing a sample in a solution liquid into a nanofluidic channel and passing the sample through at least one nanogap detector associated with the nanofluidic channel. The nanogap detector includes a nanogap for constraining the sample and limiting the number of molecules within the measurement site. Changes are then observed in environmental characteristics within the nanogap, responsive to the passage of the sample through the nanogap.

In an alternate embodiment, the present disclosure presents a measurement device for analyzing samples consisting of single molecules, small particles, or small quantities of matter. The molecular measurement device includes at least one nanofluidic channel through which a solution containing a sample to be analyzed can be drawn, and which is configured to constrain the sample in a linear configuration. At least one nanogap detector is associated with the nanofluidic channel. The nanogap detector consists of a pair of detector elements defining a nanogap across the nanofluidic channel through which the sample is passed. The nanogap detector provides an output representative of an environmental condition within the nanogap which changes in response to the presence of a sample within the nanogap.

In a further embodiment, the present disclosure provides a method for the manufacture of a detector suitable for manipulating, detecting, and/or analyzing single molecules, single small particles, or single small samples of matter. The method includes the steps of providing a substrate; forming at least a single nanofluidic channel on said substrate; disposing a resist layer over said substrate; fabricating at least a single trench in said resist layer, said single trench aligned normal to said nanofluidic channel; utilizing said trench in the formation of metallic nanowires and a nanogap within said nanofluidic channel by a metal lift-off procedure; removing any residual resist layer; and optionally sealing said nanofluidic channel, said nanowires, and said nanogap with a cover.

The present disclosure can be embodied in-part in the form of computer-implemented processes and apparatuses for practicing those processes. The present disclosure can also be embodied in-part in the form of computer program code containing instructions embodied in tangible media or computer readable storage medium, wherein, when the computer program code is loaded into, and executed by, an electronic device such as a computer, micro-processor or logic circuit, the device becomes an apparatus for practicing the present disclosure.

The present disclosure can also be embodied in-part in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the present disclosure. When implemented in a general-purpose microprocessor, the computer program code segments configure the microprocessor to create specific logic circuits.

As various changes could be made in the above constructions without departing from the scope of the disclosure, it is intended that all matter contained in the above description or shown in the accompanying drawings shall be interpreted as illustrative and not in a limiting sense.

The invention claimed is:

1. A method for measuring a property of a sample in a solution comprising:

drawing a solution that contains a sample into a nanofluidic channel that has a nanogap detector positioned inside or adjacent to the nanofluidic channel, wherein the nanofluidic channel has a geometry with a width, a height and a length that confines and stretches the sample within the channel, and wherein the nanogap detector comprises two electrodes separated by a gap that is equal to or less than 20 nm;

passing the sample through the gap of the nanogap detector; and measuring an electrical output from the nanogap detector responsive to the passing of the sample through said gap, wherein the output is a representative of a property of the sample, and wherein the sample comprises single molecules, single small particles, or small quantities of matter.

2. The sampling method of claim 1 wherein said nanogap detectors comprises a plurality of nanogap detectors forming a plurality of gaps and wherein the sample is passed through the plurality of gaps spaced apart from each other along a length of said nanofluidic channel, and wherein each of said plurality of nanogap detectors measures one or more properties of the sample responsive to said passage of the sample thereby and each provides the output representative of at least one of the properties.

3. The sampling method of claim 2 wherein said property is measured by an electrical signal, wherein said property includes the existence, length, and flow speed of the sample as the sample passes through the gap of the spaced apart nanogap detectors.

4. The sampling method of claim 1 wherein said step of measuring an electrical output includes measuring electrical conductance, and/or electrical capacitance.

5. The sampling method of claim 1 wherein said nanogap detector is positioned inside the nanofluidic channel.

6. The sampling method of claim 1 wherein said nanogap detector is positioned adjacent to the nanofluidic channel.

7. The sampling method of claim 1 wherein the nanogap detector is made of a material selected from the group consisting of: metals, semiconductors, carbon nanotube, silicon nanowires, semiconducting organic materials, and conducting organic materials, and any combination thereof.

8. The sampling method of claim 7 wherein said sample is a label-free single DNA strand.

9. The method of claim 1, wherein the nanogap detector is fabricated using a method selected from the group consisting of: e-beam lithography, nanoimprint lithography, focused ion beam, scanning probe lithography, photo-lithography, and any combination thereof.

10. The method of claim 1 wherein the fluidic channel has a first end and a second end, wherein drawing the sample in the solution liquid into the nanofluidic channel includes applying a pressure difference between the first end and the second end of the fluidic channel, said pressure difference providing the drawing of the sample in the solution into the nanofluidic channel and the passing of the sample through the nanogap detector.

11. The method of claim 1 wherein at least a portion of the nanogap detector is positioned within the nanofluidic channel.

12. The method of claim 1 wherein the nanofluidic channel is defined in a surface of at least one layer of a planar substrate and wherein the processes of drawing and passing include moving the sample through the channel from a first position on the surface of the substrate to a second position on the surface of the substrate.

13. The method of claim 1 wherein the property includes at least one selected from the group consisting of total contour length, elasticity, a density, and a charge density.

14. The method of claim 1 wherein the sample is a label-free single DNA strand.

15. The method of claim 1 wherein the measurement is an electrical measurement, and the property of the sample represented by an output of the measurement is the detection of the length of a single molecule.

16. The method of claim 1 wherein the measurement is an electrical measurement, and the property of the sample represented by an output of the measurement is the detection of the flow speed of a single molecule.

17. The method of claim 1 wherein the measurement is an electrical measurement, and the property of the sample represented by an output of the measurement is the detection of the molecular or atomic structures, physical and chemical function of a single molecule.

* * * * *